United States Patent
Kiaei

(10) Patent No.: US 10,203,338 B2
(45) Date of Patent: Feb. 12, 2019

(54) STABILIZED LIQUID FORMULATIONS CONTAINING RECEPTORS

(71) Applicant: SIEMENS HEALTHCARE DIAGNOSTICS INC., Tarrytown, NY (US)

(72) Inventor: David Kiaei, Roslyn Heighs, NY (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/891,269

(22) PCT Filed: May 13, 2014

(86) PCT No.: PCT/US2014/037909
§ 371 (c)(1),
(2) Date: Nov. 13, 2015

(87) PCT Pub. No.: WO2014/186402
PCT Pub. Date: Nov. 20, 2014

(65) Prior Publication Data
US 2016/0084847 A1 Mar. 24, 2016

Related U.S. Application Data

(60) Provisional application No. 61/823,116, filed on May 14, 2013.

(51) Int. Cl.
*G01N 33/78* (2006.01)
*G01N 33/53* (2006.01)
*G01N 33/68* (2006.01)
*C07K 14/72* (2006.01)

(52) U.S. Cl.
CPC ....... *G01N 33/6854* (2013.01); *C07K 14/723* (2013.01); *G01N 33/5306* (2013.01); *G01N 33/78* (2013.01); *G01N 2333/726* (2013.01)

(58) Field of Classification Search
CPC ............. C07K 14/723; G01N 33/5306; G01N 33/6854; G01N 33/78; G01N 2333/726
See application file for complete search history.

(56) References Cited

U.S. PATENT DOCUMENTS

| 2003/0099608 A1 | 5/2003 | Presnell et al. |
| 2008/0305098 A1 | 12/2008 | Fenning et al. |
| 2009/0325310 A1* | 12/2009 | Loos .................... C07K 14/723 436/500 |

FOREIGN PATENT DOCUMENTS

| JP | S61-005094 A | 1/1986 | |
| JP | S61-141900 A | 6/1986 | |
| JP | 2000-502357 A | 2/2000 | |
| JP | 2006-519754 A | 8/2006 | |
| JP | 2011-136911 A | 7/2011 | |
| JP | 2010-230660 A | 10/2014 | |
| WO | WO 9746206 A2 * | 12/1997 | ........... C07K 14/723 |
| WO | 2004/048415 A1 | 6/2004 | |

OTHER PUBLICATIONS

PCT Search Report and Written Opinion dated Sep. 11, 2014 for International Application No. PCT/US2014/037909, 7 pp.
Supplementary European Search Report dated Oct. 28, 2016 for European Application No. 14797839.9, 9 pp.
Wu, Ning-Ling, et al., "significance of thyrotrophic receptor antibody (TRAb) in clinical diagnosis of Graves'desease", Med. J. Chin. PLA, vol. 36, No. 5, May 1, 2011, pp. 501-504, / May 5, 2011.
Matsumoto, Hirofumi, et el., "decreased expression of the thyroid-stimulating hormone receptor in poorly-differentiated carcinoma of the thyroid", oncology reports 19, pp. 1405-1411, 2008, / Jun. 30, 2008.
Dong, Zuo-Liang, "comparison of clinical application of two detection methods of TSH-receptor antibody", journal of tianjin medical university, vol. 14, No. 3, Sep. 2008, pp. 297-302 / Sep. 1, 2008.
Vlase, H., et al., "folding-dependent binding of thyrotropin (TSH) and TSH receptor autoantibodies to the murine TSH receptor ectodomain*", vol. 138, No. 4, 1997, Dep. of medicine and pharacology (RPM), Mount Sinai school of medicine, NY 10029, 0013-7227/97/$03.00/0, Endocrinology, pp. 1658-1666/ Apr. 1, 1997.

* cited by examiner

*Primary Examiner* — Shafiqul Haq
(74) *Attorney, Agent, or Firm* — Kevin Stein

(57) ABSTRACT

Methods and reagents are disclosed for preparing a liquid solution of a receptor. The methods comprise combining in a liquid medium the receptor, a chelating agent and a C2-C6 polyol. An amount of the chelating agent and the C2-C6 polyol is sufficient to achieve a stable and active receptor in the liquid solution, which is maintained at a temperature of about 2° C. to about 40° C. The compositions may be employed in assays for the determination of analytes that include receptor-binding analytes.

5 Claims, 2 Drawing Sheets

STABILIZED LIQUID FORMULATIONS CONTAINING RECEPTORS

CROSS-REFERENCE TO RELATED APPLICATIONS

This application claims priority to U.S. Provisional Application Ser. No. 61/823,116 filed May 14, 2013, which is incorporated herein by reference in its entirety.

BACKGROUND

The invention relates to compositions, methods and kits for the determination of analytes such as, for example, antibodies, in samples, such as patient samples, known or suspected to contain one or more of such analytes. In some examples the invention relates more particularly to maintaining stability of receptor reagents during storage as liquid formulations at temperatures above freezing. In some examples the invention relates more particularly to enhancing the sensitivity of receptor reagents for use in assays for analytes.

The clinical diagnostic field has seen a broad expansion over the past 35 years or more, both as to the variety of materials of interest that may be readily and accurately determined, as well as the methods for the determination. Convenient, reliable and non-hazardous means for detecting the presence of low concentrations of materials in liquids is desired. In clinical chemistry these materials may be present in body fluids in concentrations below $10^{-12}$ molar. The difficulty of detecting low concentrations of these materials is enhanced by the relatively small sample sizes that can be utilized.

The need to determine many analytes in blood and other biological fluids has become increasingly apparent in many branches of medicine. In endocrinology the knowledge of plasma concentration of a number of different hormones is often required to resolve a diagnostic problem or a panel of markers for a given diagnosis where the ratios could assist in determining disease progression. Receptors such as hormone receptors are used commonly in a number of in vitro applications. In diagnostic assays, for example, receptors such as, for example, hormone receptors are used for detection of patient antibodies that are indicative of one or more disease states. In a particular example, thyrotropin (also known as thyroid-stimulating hormone or TSH) receptors are used in diagnostics assays for the detection of TSH receptor antibodies as an aid in the differential diagnosis of Graves' disease.

Due to their instability in liquid form, many receptors are either dried on a surface or lyophilized. These approaches are not desirable since they add manufacturing cost and are inconvenient for those who use the reagents. Furthermore, upon reconstitution for use, many such receptors still have a very short half-life.

There is, therefore, a continuing need to develop compositions comprising receptors that exhibit good stability in a liquid form and good sensitivity in an assay employing the receptors to measure levels of antibodies and other analytes in patients.

SUMMARY

Some examples in accordance with the principles described herein are directed to methods of preparing a liquid solution of a receptor. The methods comprise combining in a liquid medium the receptor, a chelating agent and a C2-C6 polyol. An amount of the chelating agent and the C2-C6 polyol is sufficient to achieve a stable and sensitive receptor in the liquid solution, which is maintained at a temperature of about 2° C. to about 40° C. during storage.

Some examples in accordance with the principles described herein are directed to methods of stabilizing a liquid solution of a thyroid stimulating hormone receptor. The method comprises combining a liquid solution comprising a thyroid stimulating hormone receptor with a stabilizing amount of both (i) a chelating agent selected from the group consisting of triacetic acid chelating agents and tetraacetic acid chelating agents and (i) a C3-C5 polyol.

Some examples in accordance with the principles described herein are directed to compositions comprising an aqueous medium, a receptor chimera, a chelating agent in an amount of about 0.1 mM to about 20 mM, and a C2-C6 polyol in an amount of about 5% to about 50% by weight.

Some examples in accordance with the principles described herein are directed to methods of detecting a thyroid stimulating hormone receptor antibody in a sample. A combination is provided in an assay medium where the combination comprises a sample suspected of containing a thyroid stimulating hormone receptor antibody, a first thyroid stimulating hormone receptor bound to a support and a second thyroid stimulating hormone receptor bound to a label. Either or both of the first and second thyroid stimulating hormone receptors are from compositions stored in accordance with the principles described herein. The combination is examined for the formation of a complex comprising the thyroid stimulating hormone receptor antibody. The presence of the complex is related to one or both of a presence and an amount of the thyroid stimulating hormone receptor antibody in the sample.

BRIEF DESCRIPTION OF THE DRAWINGS

The drawings provided herein are not to scale and are provided for the purpose of facilitating the understanding of certain examples in accordance with the principles described herein and are provided by way of illustration and not limitation on the scope of the appended claims.

DETAILED DESCRIPTION

General Discussion

Figure 1:
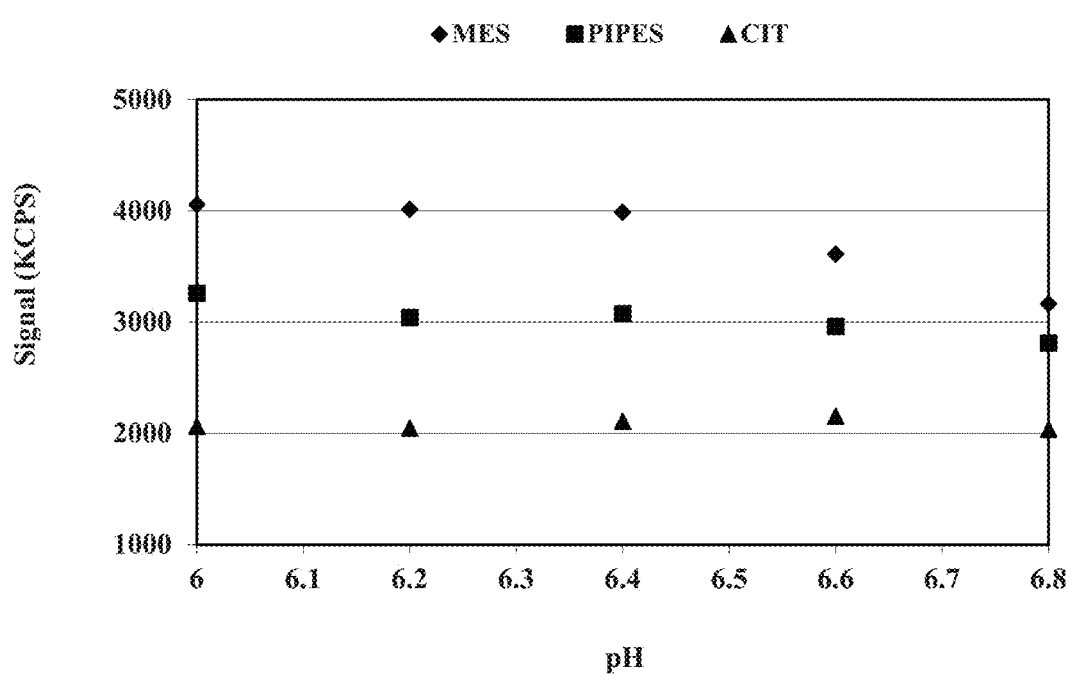
FIG. 1 is a graph depicting a plot of signal versus pH for a receptor chimera conjugated to alkaline phosphatase (the "conjugate") upon dissolution in citrate buffer in an example of a method in accordance with the principles described herein and also, for purposes of comparison, upon dissolution of the conjugate in MES and PIPES buffers, respectively.

The disclosure in accordance with the principles described herein provides methods of preparing liquid formulations of receptors that may be stored for extended periods of time while maintaining the stability of the receptor. In addition, the present inventors have discovered that the sensitivity of receptors prepared in accordance with the principles described herein is enhanced over that of receptors subjected to drying or lyophilization and subsequent reconstitution. As mentioned above, some examples in accordance with the principles described herein are directed to methods of preparing a liquid solution of a receptor, storage of such liquid solutions, and use of such liquid solutions in assays for detection of analytes of interest.

Detailed Discussion

The term "receptor" as used herein refers to compounds that bind with a substance (sometimes referred to as a ligand) for which they are structurally specific. The receptors have an area on the surface or in a cavity, which specifically binds to and is thereby defined as complementary with a particular spatial and polar organization of another molecule sometimes referred to as a ligand. Ligands may be small molecules including, but not limited to, drugs, small peptides, or steroids, for example, or large molecules such as large peptides, proteins including antibodies, hormones, DNA, RNA, carbohydrates, for example, and including portions or regions thereof. By way of illustration and not limitation, receptors include hormone receptors, drug receptors, and antigen receptors, for example. The receptor may be an intact or complete receptor or a fragment or segment thereof. Fragments or segments may be prepared by subjecting an intact receptor to fragmentation techniques. On the other hand, fragments or segments of receptors, as well as intact or complete receptors, may be prepared synthetically. Thus, the receptor may be naturally occurring and isolated from a source or the receptor may be synthetic and prepared by synthetic techniques that include, but are not limited to, recombinant techniques and chimeric techniques, for example.

In some examples the receptors are those that are specific for antibodies such as, for example, autoantibodies that are associated with certain disease states, which include, but are not limited to, dermatomyositis, diabetes mellitus, epilepsy, Kawasaki's disease, glomerulonephritis, Graves' disease, Goodpasture's syndrome, Guillain-Barre syndrome, inflammatory bowel disease, Lupus nephritis, multiple sclerosis, myasthenia gravis, myocarditis, Parkinson disease, pemphigus, pernicious anemia, polyarteritis nodosa, polymyositis, primary biliary cirrhosis, psoriasis, rheumatic fever, rheumatoid arthritis, sarcoidosis, scleroderma, sjogren's syndrome, systemic lupus erythematosus, thyroiditis, ulcerative colitis, uveitis, vitiligo, Wegener's granulomatosis, and Wilsons diseases, for example.

In an example in accordance with the principles described herein, by way of illustration and not limitation, the receptor is a TSH receptor and the autoantibodies are TSH autoantibodies. In another example in accordance with the principles described herein, by way of illustration and not limitation, the receptor is a TSH receptor chimera and the autoantibodies are TSH autoantibodies. In another example in accordance with the principles described herein, by way of illustration and not limitation, the receptors are TSH receptor chimeras, examples of which are disclosed in U.S. Patent Application Publication No. 2009/0325310 A1 (Loos) published Dec. 31, 2009, and the autoantibodies are TSH autoantibodies.

The term "receptor" also includes receptors bound to or attached to a conjugative moiety. Receptor conjugates comprise a receptor and a conjugative moiety bound together, optionally through a linking group, to form a single structure. The binding can be the result of either covalent attachment or non-covalent attachment. Covalent attachment involves a direct connection, e.g., a chemical bond between a receptor and a conjugative moiety or between a receptor and a conjugative moiety through the intermediacy of a linking group. Non-covalent attachment involves specific binding between complementary specific binding pair (sbp) members that are attached to a receptor and a conjugative moiety of the conjugate.

The conjugative moiety is any entity that may be conjugated to a receptor to form a reagent that is employed in an assay for the detection of the receptor or an entity to which the receptor binds (receptor-binding analyte). Conjugative moieties include, by way of illustration and not limitation, supports, members of a signal producing system, members of binding pairs such as, for example, ligands and receptors (e.g., biotin-streptavidin or fluorescein-anti-fluorescein antibodies), and macromolecules that provide anchors to a drug analog, for example.

A support may be comprised of an organic or inorganic, solid or fluid, water insoluble material, which may be transparent or partially transparent. The support may be synthetic or naturally-occurring. The support can have any of a number of shapes, such as particle, including bead, film, membrane, tube, well, strip, rod, planar surfaces such as, e.g., plate, paper, etc., fiber, and the like. Depending on the type of assay, the support may or may not be suspendable in the medium in which it is employed. Examples of suspendable supports are polymeric materials such as latex, lipid bilayers or liposomes, oil droplets, cells and hydrogels, metallic particles, and magnetic particles, for example. Other support compositions include polymers, such as cross-linked polysaccharides including agarose and dextran, for example, cellulose, nitrocellulose, cellulose acetate, polyvinyl alcohol, poly(vinyl chloride), polyacrylamide, polyacrylate, polymethacrylates, polyethylene, polypropylene, poly (4-methylbutene), polystyrene, polymethacrylate, poly (ethylene terephthalate), nylon, and poly(vinyl butyrate), for example, either used by themselves or in conjunction with other materials.

The support may be a particle. The particles may have an average diameter of at least about 0.02 microns and not more than about 100 microns. In some embodiments, the particles have an average diameter from about 0.05 microns to about 20 microns, or from about 0.3 microns to about 10 microns. The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, *streptococcus, Staphylococcus aureus, E. coli*, and viruses, for example. The particles can also be comprised of organic and inorganic polymers, liposomes, latex particles, metallic particles, magnetic or non-magnetic particles, phospholipid vesicles, chylomicrons, and lipoproteins, for example. In some examples, the particles are latex particles or chromium dioxide (chrome) particles. In some examples, the particles are readily dispersible in an aqueous medium and can be adsorptive or functionalizable so as to permit conjugation to a receptor, either directly or indirectly through a linking group.

Specific signal producing systems and labels are discussed in more detail hereinbelow in the discussion of various assay systems to which examples in accordance with the principles described herein may be applied. Briefly, a signal producing system (sps) may have one or more components or members, at least one component or member being a label, which is capable of being detected directly or is detectable through a specific binding reaction that produces a detectable signal. The signal producing system generates a signal that relates to the presence of a receptor or a receptor-binding analyte in a sample. The signal producing system includes all of the reagents required to produce a measurable signal. Other components of the signal producing system may be included in a developer solution and can include substrates, enhancers, activators, chemiluminescent compounds, cofactors, inhibitors, scavengers, metal ions, and specific binding substances required for binding of signal generating substances, for example. Other components of the signal producing system may be coenzymes, substances that react with enzymic products, other enzymes and catalysts, for example. The signal producing system provides a signal detectable by external means, by use of electromagnetic radiation, desirably by visual examination. Exemplary signal-producing systems are described in U.S. Pat. No. 5,508,178 (Rose, et al.) and Ullman, et al., U.S. Pat. No. 5,185,243, columns 11-13, the relevant disclosure of which is incorporated herein by reference.

For covalent attachment of the components of a conjugate, that is a receptor and a conjugative moiety, one or more of the components contains a functional group suitable for attachment to one or more of the other components. The functional groups suitable for attaching the components may be carbonyl functionalities, both oxocarbonyl, e.g., aldehyde, and non-oxocarbonyl (including nitrogen and sulfur analogs) e.g., carboxy, amidine, amidate, thiocarboxy and thionocarboxy. Alternative functionalities of oxo include active halogen, diazo, mercapto, olefin, particularly activated olefin, amino, phosphoro and the like. Of particular interest are activated esters or alkylating agents. Details of techniques for attaching molecules to one another may be found, for example, in Matthews, et al., *Anal. Biochem.* (1985) 151:205-209; Engelhardt, et al., European Patent Application No. 0302175 and U.S. Pat. No. 3,817,837, the relevant disclosure of which is incorporated herein by reference in its entirety.

As mentioned above, covalent attachment may be achieved through the intermediacy of a linking group. The linking group may be a chain of from 1 to about 50 or more atoms, or from 1 to about 30 or more atoms, from about 1 to about 20 atoms, from 1 to about 10 atoms, each independently selected from the group normally consisting of carbon, oxygen, sulfur, nitrogen, and phosphorous, usually carbon and oxygen. The number of heteroatoms in the linking group may range from 0 to about 10 or more, or from 0 to about 8, from 1 to about 6, from 2 to about 4. The number of atoms in the chain is determined by counting the number of atoms other than hydrogen or other monovalent atoms along the shortest route between the substructures being connected. The atoms of the linking group may be substituted with atoms other than hydrogen such as carbon, oxygen and so forth in the form, e.g., of alkyl, aryl, aralkyl, hydroxyl, alkoxy, aryloxy, and aralkoxy, for example. As a general rule, the length of a particular linking group can be selected arbitrarily to provide for convenience of synthesis with the proviso that there be minimal interference caused by the linking group with the ability of the compounds to be linked together. The linking group may be aliphatic or aromatic. Functionalities present in the linking group may include esters, thioesters, amides, thioamides, ethers, ureas, thioureas, guanidines, azo groups, thioethers, carboxylate and so forth.

As indicated above, the components, i.e., receptor and conjugative moiety, of receptor-moiety conjugates may be attached together non-covalently. For example, a small organic molecule such as, but not limited to, biotin including bis-biotin, and fluorescein, for example, may be incorporated into one of the components and the other component may be linked to a binding partner for the small organic molecule such as, for example, respectively, avidin (streptavidin) or anti-fluorescein. The binding of the binding partners results in the non-covalent attachment of the components to one another.

Methods in accordance with the principles described herein comprise combining in a liquid medium the receptor and effective amounts of a chelating agent and a C2-C6 polyol. In some examples in accordance with the principles described herein, the chelating agent may be, but is not limited to, N-(2-hydroxyethyl)-ethylenediamine-N,N',N'-triacetic acid (HEDTA), ethylenediamine-tetraacetic acid (EDTA), trans-1,2-diamino-cyclohexan-N,N,N',N'-tetraacetic acid (CDTA), ethylene glycol-O,O'-bis-(2-aminoethyl)-N,N,N',N'-tetraacetic acid (EGTA), diethylenetriamine-pentaacetic acid (DTPA), nitrilotriacetic acid (NTA), nitrilo-2,2',2"-triacetic acid, diethylenetriamine-N,N,N',N', N"-pentaacetic acid, triethylenetetramin-N,N,N',N",N''',N'''-hexaacetic acid (TTHA), methylamine, histidine, malate and phytochelatin, hemoglobin, chlorophyll, siderophore, pyocyanin, pyoverdin, Enterobactin, peptides and sugars, humic acid, citric acid, water softeners, phosphonates, tetracycline, gadolinium, organophosphorus compound 2,2'-bis(diphenylphosphino)-1,1'-binaphthyl, pentetic acid; N,N-Bis(2-(bis-(carboxymethyl)amino)ethyl)-glycine, N,N-bis(carboxymethyl)glycine, triglycollamic acid; [(Carboxymethyl) imino]bis-(ethylenenitrilo)]-tetraacetic acid), Trilone A, $\alpha,\alpha',\alpha''$-trimethylaminetricarboxylic acid, tri(carboxymethyl)amine, aminotriacetic acid, Titriplex i, and Hampshire NTA acid, for example, and appropriate salts of any of the above.

In some examples in accordance with the principles described herein, the chelating agent comprises a triacetic acid moiety or a salt thereof, a tetraacetic acid moiety or a salt thereof, a pentaacetic acid moiety or a salt thereof, or a hexaacetic acid moiety or a salt thereof. In some examples, the chelating agent is selected from the group consisting of N-(2-hydroxyethyl)-ethylenediamine-N,N',N'-triacetic acid and its salts, ethylene diamine tetraacetic acid and its salts, and ethylene glycol tetraacetic acid and its salts. In some examples, the chelating agent is a citric acid or a salt thereof.

In some examples in accordance with the principles described herein, the number of carbon atoms in the polyol is 2 to 8, or 2 to 7, or 2 to 6, or 2 to 5, or 2 to 4, or 2 to 3, or 3 to 8, or 3 to 7, or 3 to 6, or 3 to 5, or 3 to 4, or 4 to 8, or 4 to 7, or 4 to 6, or 4 to 5, for example, and the number of hydroxyl groups is about 1 per carbon atom, or 1 per 2 carbon atoms, or 1 per 3 carbon atoms, or 2 per 2 carbon atom, or 2 per 3 carbon atoms, for example, with the total number of hydroxyl groups in the polyol being about 2, or about 3, or about 4, or about 5, or about 6, or about 7, or about 8, for example. In some examples, by way of illustration and not limitation, the polyol is a $C_2$, or $C_3$, or $C_4$, or $C_5$, or $C_6$ polyol comprising 2 hydroxy groups or 3 hydroxy groups, or 4 hydroxyl groups, or 5 hydroxyl groups, or 6 hydroxyl groups such as, by way of illustration and not limitation, ethylene glycol, propylene glycol, glycerol, erythritol, xylitol, ribitol, and sorbitol, for example. The polyol may be a single compound or a combination of two or more polyols having the aforementioned properties. In some examples in accordance with the principles described herein, the polyol is glycerol.

The chelating agent and the polyol are present in the combination in amounts that are effective to stabilize the receptor and/or to enhance the sensitivity of the receptor. The amount of the chelating agent and the amount of the polyol are dependent on one or more of the nature and amount of the receptor, the nature of the chelating agent, the nature of the polyol, and the nature of the liquid formulation, for example. In some examples in accordance with the principles described herein, an effective amount of the chelating agent in the combination may be, for example, about 0.1 mM to about 20 mM, or about 1 mM to about 20 mM, or about 5 mM to about 20 mM, or about 10 mM to about 20 mM, or about 10 mM to about 15 mM, or about 15 mM to about 20 mM or about 1 to about 5 mM.

In some examples in accordance with the principles described herein, an effective amount of the polyol in the combination may be, for example, about 5% to about 50%, or about 5% to about 40%, or about 5% to about 30%, or about 5% to about 20%, or about 5% to about 10%, or about 10% to about 50%, or about 10% to about 40%, or about 10% to about 30%, or about 10% to about 20%, for example. The above percentages are by weight of the polyol in a liquid medium.

Some examples in accordance with the principles described herein are directed to compositions comprising an aqueous medium, a receptor, a chelating agent in an amount of about 0.1 mM to about 20 mM, and a C2-C6 polyol in an amount of about 5% to about 50% by weight.

In some examples, the liquid medium or liquid solution is an aqueous medium, which may be solely water or may include about 0.1% to about 80%, or 0.1% to about 60%, or about 0.1 to about 40%, or about 0.1% to about 30%, or about 0.1% to about 20%, or about 0.1% to about 10%, or about 0.1% to about 5%, or about 1% to about 80%, or 1% to about 60%, or about 1% to about 40%, or about 1% to about 30%, or about 1% to about 20%, or about 1% to about 10%, or about 1% to about 5%, or about 5% to about 80%, or 5% to about 60%, or about 5% to about 40%, or about 5% to about 30%, or about 5% to about 20%, or about 5% to about 10%, for example, of a cosolvent. The above percentages are by volume of the medium. The cosolvent may be, for example, but not limited to, an organic solvent such as, for example, an alcohol, an ester, an ether, an amide or an amine.

The pH for the medium will usually be in the range of about 4 to about 11, or in the range of about 5 to about 10, or in the range of about 6.5 to about 9.5, or in the range of about 6.5 to about 7.5, or about 7, for example. Various buffers may be used to achieve the desired pH and maintain the pH of the medium. Illustrative buffers include borate, phosphate, carbonate, tris, and barbital, for example. The particular buffer employed is not critical, but in an individual composition one or another buffer may be preferred. Various ancillary materials also may be included in the medium. For example, in addition to buffers the medium may contain preservatives, non-specific binding blockers and heterophilic interference blockers to prevent false results, and surfactants, for example.

The liquid solution of the receptor, the chelating agent and the C2-C6 polyol may be maintained at a temperature of about 2° C. to about 40° C., or about 2° C. to about 30° C., or about 2° C. to about 20° C., or about 5° C. to about 40° C., or about 5° C. to about 30° C., or about 5° C. to about 20° C., or about 5° C. to about 10° C., or about 10° C. to about 40° C., or about 10° C. to about 30° C., or about 10° C. to about 20° C., or about 15° C. to about 40° C., or about 15° C. to about 30° C., or about 15° C. to about 20° C., or about 20° C. to about 25° C., or about ambient temperature, for example. The liquid solution of the receptor maintains good stability for at least about 1 week, or at least about 1 month, or at least about 6 months, or at least about 1 year, or at least about 1.5 years, or at least about 2 years, for example. The phrase "good stability" as used herein means that the receptor does not lose more than about 40%, or more than about 30%, or more than about 20%, or more than about 10%, or more than about 5% of its activity over a period of 12 months or that the receptor has a half-life of at least about 12 months, or at least about 15 months, or at least about 20 months during storage at a temperature of about 2° C. to about 10° C.

The compositions in accordance with the principles described herein may be employed in methods of detecting in a sample a receptor-binding analyte, which refers to a molecule that binds to the receptor. The sample to be analyzed is one that is suspected of containing one or more receptor-binding analytes. The samples are preferably from humans or animals and include, but are not limited to, biological fluids such as whole blood, serum, plasma, sputum, lymphatic fluid, semen, vaginal mucus, feces, urine, spinal fluid, saliva, stool, cerebral spinal fluid, tears, and mucus, for example, and biological tissue such as hair, skin, sections or excised tissues from organs or other body parts, for example. In many instances, the sample is whole blood, plasma or serum and, in a particular example, the sample is serum. The sample may or may not be pretreated to remove endogenous binding moieties that bind to the receptor-binding analyte or to release the receptor-binding analyte from endogenous binding substances.

The sample can be prepared in any convenient medium that does not interfere with an assay; an aqueous medium generally is employed. The nature of the medium is discussed in more detail below. Depending on the nature of the sample, one or more pretreatments may be carried out on the sample such as, by way of illustration and not limitation, pretreatment with a hemolytic agent, pretreatment with a releasing agent, pretreatment with a displacer that displaces bound receptor-binding analyte from its endogenous binding partners such as proteins, and hemolytic detergent(s) that assist in lysing blood cells to release a receptor-binding analyte from blood cells, for example. Any of the above agents are present in a concentration or amount sufficient to achieve the desired effect or function, such as, for example, hemolysis or release of receptor-binding analyte from endogenous binding substances.

Following the above pretreatment, if any, reagents for determining one or both of the presence and amount of the receptor-binding analyte in the sample are added to the medium. The nature of the reagents is dependent on the particular type of assay to be performed. In general, the assay is a method for the determination or measuring of one or both of the presence and amount of a receptor-binding analyte. Various assay methods are discussed below by way of illustration and not limitation.

In some examples in accordance with the principles described herein, the assay reagents include at least one receptor for the receptor-binding analyte. The receptor is present in a liquid composition or liquid solution in accordance with the principles described herein and a portion of the liquid composition is combined in the assay medium. As mentioned above, receptors treated with a combination of a polyol and a chelating agent in accordance with the principles described herein also exhibit enhanced sensitivity over receptors that were not treated in this manner. The phrase "enhanced sensitivity" means that the sensitivity achieved in an assay for a receptor-binding analyte that employs a receptor treated in accordance with the principles described herein is at least about 10% greater, or at least about 25% greater, or at least about 50% greater, or at least about 75% greater than the sensitivity of an assay using a receptor not treated in accordance with the principles described herein.

In addition to one or more receptors, assay reagents may include one or more antibodies specific for a receptor, or for a receptor-binding analyte, another antibody, or a small molecule, for example. Antibodies can be monoclonal or polyclonal. Such antibodies can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, and IgM, for example. Fragments thereof may include Fab, Fv and F(ab')$_2$, and Fab', for example. In addition, aggregates, polymers, and conjugates of immunoglobulins or their fragments can be used where appropriate so long as binding affinity for a particular molecule is maintained.

Other reagents are included in an assay medium depending on the nature of the assay to be conducted. Such assays usually involve reactions between binding partners such as a receptor and a receptor-binding analyte and may also include binding between an antibody and a corresponding binding partner such as, for example, a receptor, depending on the particular assay format chosen.

As discussed above, specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules. In some examples, the binding partners are antibodies.

General Discussion of Assays

The present disclosure has application to many types of assays that may be employed to determine one or both of the presence and amount of one or more analytes that include, for example, receptor-binding analytes, in a sample suspected of containing such analyte. The receptor reagents in accordance with the principles described herein may be employed in many assay formats that are designed for antibody reagents. The assays may involve labeled or non-labeled reagents. Assays involving non-labeled reagents usually comprise the formation of relatively large complexes involving one or more receptors. Such assays include, for example, immunoprecipitin and agglutination methods and corresponding light scattering techniques such as, e.g., nephelometry and turbidimetry, for the detection of receptor complexes. For non-labeled assays, a composition in accordance with the principles described herein may be employed where the composition comprises a conjugate of a receptor-binding analyte and a support such as, for example, a particle. In one example, the receptor-binding analyte in a sample competes with the receptor-binding analyte-support conjugate such that the more the amount of receptor-binding analyte in a sample, the less will be the amount of a precipitate formed by agglutination. In some examples the receptor-binding analyte is an antibody such as, for example, an autoantibody that may be present in a sample and a conjugate in accordance with the principles described herein having a receptor-binding analyte bound to a particulate support is employed. The presence of the antibody in the sample results in the agglutination of the conjugate reagent.

Labeled immunoassays include enzyme immunoassays, fluorescence polarization immunoassays, radioimmunoassay, inhibition assays, and induced luminescence, fluorescent oxygen channeling assay, for example. In one example of a labeled assay approach, a conjugate having a receptor-binding analyte bound to a label such as, for example, an enzyme, can compete with receptor-binding analyte in a sample such that the greater the amount of receptor-binding analyte in the sample, the less will be the amount of signal from the label. In another example of a labeled assay approach, a conjugate having a receptor bound to a label such as, for example, an enzyme, can be employed to bind with receptor-binding analyte in a sample and a second receptor for the receptor-binding analyte is employed to form a sandwich complex. An amount of signal from the label is detected and related to the amount of the receptor-binding analyte in the sample such that the greater the amount of receptor-binding analyte in the sample, the greater will be the amount of signal from the label.

As mentioned above, in many of the assays discussed herein, a label is employed and is in many examples part of a receptor-binding analyte conjugate. On the other hand the label may be part of a reagent independent of the receptor-binding analyte conjugate. The label is usually part of a signal producing system ("sps"). The nature of the label is dependent on the particular assay format. As discussed above, the signal producing system usually includes one or more components, at least one component being a detectable label, which generates a detectable signal that relates to the amount of bound and/or unbound label, i.e. the amount of label bound or not bound to the receptor-binding analyte being detected or to an agent that reflects the amount of the receptor-binding analyte to be detected.

The label is any molecule that produces or can be induced to produce a signal. The label can be a poly(amino acid), or protein, or non-poly(amino acid), isotopic or non-isotopic, usually non-isotopic, and can be a catalyst, such as an enzyme, a polynucleotide coding for a catalyst, promoter, dye, fluorescent molecule, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, for example. In some examples, the labels are radioisotopic, luminescent, particulate or enzymic and may be, for example, a fluorescer, radiolabel, enzyme, chemiluminescer or photosensitizer. Thus, for example, for the above labels, the signal is detected and/or measured by detecting enzyme activity, luminescence, light absorbance or radioactivity, as the case may be.

The term "non-poly(amino acid) labels" refers to those labels that are not proteins. A non-poly(amino acid) label may be a member of a signal producing system. The non-poly(amino acid) label is capable of being detected directly or is detectable through a specific binding reaction that produces a detectable signal. The non-poly(amino acid) labels generally are radioisotopic, luminescent (such as, e.g., acridinium esters), particulate (such as, e.g., magnetic particles that can be separated bound from un-bound, latex particles that can be measured by turbidity and nephelometry, and chemiluminescence beads (e.g., LOCI chemibeads), for example. The label can be isotopic or non-isotopic, usually non-isotopic, and can be a polynucleotide coding for a catalyst, promoter, dye, fluorescent molecule, chemiluminescent molecule, coenzyme, enzyme substrate, radioactive group, a small organic molecule, amplifiable polynucleotide sequence, a particle such as, e.g., latex or carbon particle, metal sol, crystallite, liposome, or cell, which may or may not be further labeled with a dye, catalyst or other detectable group, for example. Poly(amino acid) labels include, by way of illustration and not limitation, peptides and proteins such as e.g., enzymes, for example.

Examples of labels include, by way of illustration and not limitation, enzymes such as alkaline phosphatase ("AP"), glucose-6-phosphate dehydrogenase ("G6PDH") and horseradish peroxidase; ribozyme; a substrate for a replicase such as QB replicase; promoters; dyes; fluorescers, such as fluorescein, isothiocyanate, rhodamine compounds, phycoerythrin, phycocyanin, allophycocyanin, o-phthaldehyde, and fluorescamine; complexes such as those prepared from CdSe and ZnS present in semiconductor nanocrystals known as Quantum dots; chemiluminescers such as isoluminol; sensitizers; coenzymes; enzyme substrates; radiolabels such as $^{125}I$, $^{131}I$, $^{14}C$, $^{3}H$, $^{57}Co$ and $^{75}Se$; particles such as latex particles, carbon particles, metal particles including magnetic particles, e.g., chromium dioxide ($CrO_2$) particles, and the like; metal sol; crystallite; liposomes; cells, etc., which may be further labeled with a dye, catalyst or other detectable group. Suitable enzymes and coenzymes are disclosed in Litman, et al., U.S. Pat. No. 4,275,149, columns 19-28, and Boguslaski, et al., U.S. Pat. No. 4,318,980, columns 10-14; suitable fluorescers and chemiluminescers are disclosed in Litman, et al., U.S. Pat. No. 4,275,149, at columns 30 and 31; which are incorporated herein by reference.

The label can directly produce a signal and, therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal. Such other components may include substrates, coenzymes, enhancers, additional enzymes, substances that react with enzymic products, catalysts, activators, cofactors, inhibitors, scavengers, metal ions, and a specific binding substance required for binding of signal generating substances.

In some examples, enzymes of interest as label proteins are redox enzymes, particularly dehydrogenases such as glucose-6-phosphate dehydrogenase, lactate dehydrogenase, etc., and enzymes that involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations are known in the art. When a single enzyme is used as a label, other enzymes may find use such as hydrolases, transferases, and oxidoreductases, preferably hydrolases such as alkaline phosphatase and beta-galactosidase. Alternatively, luciferases may be used such as firefly luciferase and bacterial luciferase. Illustrative co-enzymes that find use include NAD[H], NADP[H], pyridoxal phosphate, FAD[H], FMN[H], etc., usually coenzymes involving cycling reactions. See, for example, U.S. Pat. No. 4,318,980, the disclosure of which is incorporated herein by reference.

One general group of assays that may be employed includes assays using a limited concentration of receptor. Another group of assays involves the use of an excess of one or more of the principal reagents such as, for example, an excess of a receptor for the receptor-binding analyte. Another group of assays are separation-free homogeneous assays in which the labeled reagents modulate the label signal upon receptor-binding analyte-receptor binding reactions. Another group of assays includes labeled receptor reagent limited competitive assays for a receptor-binding analyte. In this type of assay, a receptor-support conjugate in accordance with the principles described herein is present in a constant, limited amount. The partition of a label between the immobilized receptor-binding analyte and free receptor-binding analyte depends on the concentration of receptor-binding analyte in the sample.

The assays can be performed either without separation (homogeneous) or with separation (heterogeneous) of any of the assay components or products. Receptors in accordance with the principles described herein can be employed in many immunoassay formats. In a homogeneous assay after all of the reagents have been combined, the signal is determined and related to the amount of receptor-binding analyte in the sample. Homogeneous immunoassays are exemplified by the EMIT® assay (Syva Company, San Jose, Calif.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354,693; and so forth.

Other enzyme immunoassays are the enzyme modulate mediated immunoassay ("EMMIA") discussed by Ngo and Lenhoff, FEBS Lett. (1980) 116:285-288; the substrate labeled fluorescence immunoassay ("SLFIA") disclosed by Oellerich, J. Clin. Chem. Clin. Biochem. (1984) 22:895-904; the combined enzyme donor immunoassays ("CEDIA") disclosed by Khanna, et al., Clin. Chem. Acta (1989) 185:231-240; homogeneous particle labeled immunoassays such as particle enhanced turbidimetric inhibition immunoassays ("PETINIA"), particle enhanced turbidimetric immunoassay ("PETIA"), etc.; and the like.

Other assays include the sol particle immunoassay ("SPIA"), the disperse dye immunoassay ("DIA"); the metalloimmunoassay ("MIA"); the enzyme membrane immunoassays ("EMIA"); luminoimmunoassays ("LIA"); and so forth. Other types of assays include immunosensor assays involving the monitoring of the changes in the optical, acoustic and electrical properties of an antibody-immobilized surface upon the binding of a receptor-binding analyte. Such assays include, for example, optical immunosensor assays, acoustic immunosensor assays, semiconductor immunosensor assays, electrochemical transducer immunosensor assays, potentiometric immunosensor assays, and amperometric electrode assays.

In one example of an enzyme assay for a receptor-binding analyte, a sample suspected of containing the receptor-binding analyte is combined in an aqueous medium either simultaneously or sequentially with a receptor capable of recognizing the receptor-binding analyte and a reagent that comprises a conjugate of the receptor-binding analyte and an enzyme. The receptor is added from a liquid solution of the receptor stabilized in accordance with the principles described herein. A substrate for the enzyme is added, which results in the formation of a chromogenic or fluorogenic product upon enzyme-catalyzed reaction. Examples, by way of illustration and not limitation, of enzymes are glucose-6-phosphate dehydrogenase and alkaline phosphatase but other enzymes may be employed. The receptor-binding analyte and the receptor-binding analyte moiety of the enzyme conjugate compete for binding sites on the receptor. The enzyme activity in the medium is then determined, usually by spectrophotometric means, and is compared to the enzyme activity determined when calibrators or reference samples are tested, in which a known amount of the receptor-binding analyte is present. Typically, the calibrators are tested in a manner similar to the testing of the sample suspected of containing the receptor-binding analytes. The calibrators contain differing, but known concentrations of the receptor-binding analyte to be determined. In most examples, the concentration ranges present in the calibrators span the range of suspected receptor-binding analyte concentrations in unknown samples.

Heterogeneous assays usually involve one or more separation steps and can be competitive or non-competitive. A variety of competitive and non-competitive assay formats are disclosed in Davalian, et al., U.S. Pat. No. 5,089,390, column 14, line 25 to column 15, line 9, which disclosure is incorporated herein by reference. In one type of competitive assay, a support, as discussed herein, having a receptor for the receptor-binding analyte bound thereto is contacted with a medium containing the sample suspected of containing the receptor-binding analyte and a reagent that is a conjugate of the receptor-binding analyte and an enzyme. The support reagent with attached receptor is in a liquid solution in accordance with the principles described herein. After separating the support and the medium, the enzyme activity of the support or the medium is determined by conventional techniques and related to one or both of the presence and amount of the receptor-binding analyte in the sample. In certain examples a second enzyme may be employed in addition to the enzyme of the enzyme conjugate. The enzymes of the pair of enzymes are related in that a product of the first enzyme serves as a substrate for the second enzyme.

Another example of an assay format is a capture assay. In this assay format, the receptor for the receptor-binding analyte is covalently bound to a particle such as, for example, a magnetic particle. Alternatively, the receptor may be bound to the particle non-covalently such as, for example, by an antibody for the receptor where the antibody is covalently attached to the particle. This receptor-particle reagent is stored in a liquid solution in accordance with the principles described herein prior to its use in the assay. The sample is incubated with the receptor-particle reagent to allow the receptor-binding analyte in the sample to bind to the receptor for the receptor-binding analyte. Optionally, the particles are separated from the assay medium and washed. A reagent that comprises a conjugate of a second receptor for the receptor-binding analyte, which receptor is bound to an enzyme, is incubated with the particles. This second receptor-particle reagent may be stored in a liquid solution in accordance with the principles described herein prior to its use in the assay. After washing, the amount of enzyme that is bound to the separated particles is measured and is directly related to one or both of the presence and amount of the receptor-binding analyte in the sample.

In some embodiments multi-analyte assays may be utilized where the receptor-binding analyte may be the subject of detection along with one or more other analytes such as other receptor-binding analytes, for example. Such multi-analyte systems are described, for example, in Loor, et al., J. Anal. Toxicol. 12: 299 (1988).

The assays discussed above are normally carried out in an aqueous buffered medium at a moderate pH, generally that which provides optimum assay sensitivity. The pH for the assay medium may be in the range of about 4 to about 11, or in the range of about 5 to about 10, or in the range of about 6.5 to about 9.5, for example. The pH will usually be a compromise between optimum binding of the binding members of any specific binding pairs, the pH optimum for other reagents of the assay such as members of the signal producing system, for example.

Various buffers may be used to achieve the desired pH and maintain the pH during the determination. Illustrative buffers include borate, phosphate, carbonate, tris, barbital and the like. The particular buffer employed is not critical, but in an individual assay one or another buffer may be preferred. Various ancillary materials may be employed in the above methods. For example, in addition to buffers the medium may comprise stabilizers for the medium and for the reagents employed. Frequently, in addition to these additives, proteins may be included, such as albumins; quaternary ammonium salts; polyanions such as dextran sulfate; and binding enhancers, for example.

One or more incubation periods may be applied to the assay medium at one or more intervals including any intervals between additions of various reagents mentioned above. The medium is usually incubated at a temperature and for a time sufficient for binding of various components of the reagents to occur. Moderate temperatures are normally employed for carrying out the method and usually constant temperature, preferably, room temperature, during the period of the measurement. Incubation temperatures normally range from about 5° C. to about 99° C. or from about 15° C. to about 70° C. or from about 20° C. to about 45° C., for example. The time period for the incubation is about 0.2 seconds to about 24 hours, or about 1 second to about 6 hours, or about 2 seconds to about 1 hour, or about 1 to about 15 minutes. The time period depends on the temperature of the medium and the rate of binding of the various reagents, which is determined by the association rate constant, the concentration, the binding constant and dissociation rate constant. Temperatures during measurements will generally range from about 10° C. to about 50° C. or from about 15° C. to about 40° C., for example.

The concentration of receptor-binding analyte that may be assayed generally varies from about $10^{-5}$ to about $10^{-17}$ M, more usually from about $10^{-6}$ to about $10^{-14}$ M. Considerations, such as whether the assay is qualitative, semi-quantitative or quantitative (relative to the amount of receptor-binding analyte present in the sample), the particular detection technique and the concentration of the analyte normally determine the concentrations of the various reagents.

The concentrations of the various reagents in the assay medium will generally be determined by the concentration range of interest of the receptor-binding analyte and the nature of the assay, for example. However, the final concentration of each of the reagents is normally determined empirically to optimize the sensitivity of the assay over the range. That is, a variation in concentration of receptor-binding analyte that is of significance should provide an accurately measurable signal difference. Considerations such as the nature of the signal producing system and the nature of the receptor-binding analytes normally determine the concentrations of the various reagents.

While the order of addition may be varied widely, there will be certain preferences depending on the nature of the assay. The simplest order of addition is to add all the materials simultaneously and determine the effect that the assay medium has on the signal as in a homogeneous assay. Alternatively, the reagents can be combined sequentially. In some examples, an incubation step may be involved subsequent to each addition as discussed above.

Examination Step

In a next step of an assay method, the medium is examined for the presence of a complex comprising the receptor-binding analyte and the receptor for the receptor-binding analyte. The presence and/or amount of the complex indicates the presence and/or amount of the receptor-binding analyte in the sample.

The phrase "measuring the amount of a receptor-binding analyte" refers to the quantitative, semiquantitative and qualitative determination of the receptor-binding analyte. Methods that are quantitative, semiquantitative and qualitative, as well as all other methods for determining the receptor-binding analyte, are considered to be methods of measuring the amount of the receptor-binding analyte. For example, a method, which merely detects the presence or absence of the receptor-binding analyte in a sample suspected of containing the receptor-binding analyte, is considered to be included within the scope of the present invention. The terms "detecting" and "determining," as well as other common synonyms for measuring, are contemplated within the scope of the present invention.

In many embodiments the examination of the medium involves detection of a signal from the medium. One or both of the presence and amount of the signal are related to the presence and/or amount of the receptor-binding analyte in the sample. The particular mode of detection depends on the nature of the signal producing system. As discussed above, there are numerous methods by which a label of a signal producing system can produce a signal detectable by external means, desirably by visual examination, and include, for example, electromagnetic radiation, electrochemistry, heat, radioactivity detection, and chemical reagents.

Activation of a signal producing system depends on the nature of the signal producing system members. For those members of a signal producing system that are activated with light, the member is irradiated with light. Other activation methods will be suggested to those skilled in the art in view of the disclosures herein. For some signal producing systems, no agent for activation is necessary such as those systems that involve a label that is a radioactive label or an enzyme, for example. For enzyme systems, addition of a substrate and/or a cofactor may be necessary.

The examination for the presence and/or amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, actinometer, or photographic instrument, for example. The presence and amount of signal detected is related to the presence and amount of the receptor-binding analyte present in a sample. Temperatures during measurements generally range from about 10° C. to about 70° C. or from about 20° C. to about 45° C., or about 20° C. to about 25° C., for example. In one approach standard curves are formed using known concentrations of the receptor-binding analytes to be screened. As discussed above, calibrators and other controls may also be used.

Specific Embodiments of Assays

The following examples describe specific examples in accordance with the principles described herein by way of illustration and not limitation and are intended merely to describe, and not to limit, the scope of the present disclosure and the appended claims. Selection of TSH autoantibodies as the receptor-binding analyte and first and second TSH receptor chimeras is also by way of illustration and not limitation since the examples in accordance with the principles described herein have general application to detection of receptor-binding analytes in general and the use of receptors of all different types as discussed above.

In one example in accordance with the principles described herein, the assay employed is an induced luminescence assay, which is described in U.S. Pat. No. 5,340,716 (Ullman, et al.) and which disclosure is incorporated herein by reference. The reagents include two latex bead reagents and a biotinylated second TSH receptor chimera for the TSH autoantibodies. The first bead reagent is a conjugate wherein one latex bead that contains a chemiluminescent dye is bound either covalently or non-covalently to a first TSH receptor chimera for the TSH autoantibodies. In some examples, both the first TSH receptor chimera reagent and the second TSH receptor chimera reagent are separately stored in liquid solutions in accordance with the principles described herein. The second bead reagent is coated with streptavidin and contains a photosensitizer dye. In a first step, sample suspected of containing TSH autoantibodies is incubated with biotinylated second TSH receptor chimera for TSH autoantibodies, which allows TSH autoantibodies from the sample to saturate a fraction of the biotinylated TSH second receptor chimera where the fraction is directly related to the TSH autoantibodies concentration in the assay medium. In a second step, the first bead reagent, which as mentioned above is attached to a first TSH receptor chimera for the TSH autoantibodies is added and leads to the formation of bead-biotinylated TSH second receptor chimera complexes with the non-saturated fraction of the biotinylated second TSH receptor chimera. The second bead reagent is then added and binds to the biotin to form bead pair complexes. When illuminated by light at 680 nm, the second bead reagent converts dissolved oxygen in the reaction solution into the more energetic singlet oxygen form. In the bead pairs, the singlet oxygen diffuses into the first bead reagent thereby triggering a chemiluminescent reaction. The resulting chemiluminescent signal is measured at 612 nm and is a function of the concentration of TSH autoantibodies in the sample. The amount of this signal is related to the presence and or amount of TSH autoantibodies in the sample.

In another example in accordance with the present disclosure, a test sample suspected of containing TSH autoantibodies is mixed with a reagent (Reagent A) and a dry bead having an antibody for the TSH receptor chimera attached to the bead and a first TSH receptor chimera bound to the antibody of the bead. The sample, bead and Reagent A are incubated for a period of time and under conditions sufficient for some of the TSH autoantibodies in the sample to become bound to the TSH receptor chimera. The liquid reagent is separated from the bead by centrifugation and then washed. The washed bead is incubated with Reagent B containing a second TSH receptor chimera bound to alkaline phosphatase (detection receptor) for a period of time and under conditions for the detection receptor to bind to the TSH autoantibodies bound to the first TSH receptor chimera of the bead. The bead is separated from the assay medium and washed. Then, the bead is incubated with a substrate solution comprising a substrate for alkaline phosphatase and the medium is then examined for one or both of the presence and amount of signal, which is measured with a luminometer over time. The presence and/or amount of signal is related to the presence and/or amount of TSH autoantibodies in the original sample.

Kits

The reagents for conducting a particular assay may be present in a kit useful for conveniently performing an assay for the determination of a receptor-binding analyte. In one example in accordance with the principles described herein, a kit comprises in packaged combination a receptor for a receptor-binding analyte and other reagents for performing an assay for detection of the receptor-binding analyte where the nature of such reagents depends upon the particular assay format. The receptor reagent is present in a liquid solution that comprises a chelating agent and a polyol in accordance with the principles described herein. The kit can also comprise a detection receptor agent that comprises a label. The detection receptor agent is present in a liquid solution that comprises a chelating agent and a polyol in accordance with the principles described herein. The reagents may each be in separate containers or various reagents can be combined in one or more containers depending on the cross-reactivity and stability of the reagents. The kit can further include other separately packaged reagents for conducting an assay such as additional binding reagents and ancillary reagents such as an enzyme substrate reagent, for example.

The relative amounts of the various reagents in the kits can be varied widely to provide for concentrations of the reagents that substantially optimize the reactions that need to occur during the assay method and further to optimize substantially the sensitivity of the assay. Reagents other than those that contain a receptor in accordance with the principles described herein can be provided under appropriate circumstances as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

DEFINITIONS

The phrase "at least" as used herein means that the number of specified items may be equal to or greater than the number recited.

The phrase "about" as used herein means that the number recited may differ by plus or minus 10%; for example, "about 5" means a range of 4.5 to 5.5.

The designations "first" and "second" are used solely for the purpose of differentiating between two items such as, for example, "first receptor" and "second receptor," and are not meant to imply any sequence or order or importance to one item over another.

EXAMPLES

The following examples are by way of illustration and not limitation on the scope of the present disclosure and the appended claims. Numerous modifications and alternative compositions, methods, and systems may be devised without departing from the spirit and scope of the present disclosure. Unless otherwise indicated, materials in the experiments below may be purchased from Sigma-Aldrich Chemical Company, St. Louis Mo. Parts and percentages are by weight unless indicated otherwise.

The proceeding examples describe an assay and utilize a kit for the quantitative detection of Thyroid Stimulating Immunoglobulins (TSI), which are autoantibodies to TSH receptor. The measurement of TSI in serum samples is used as an aid in the assessment of patients suspected of having Graves' disease. The kit consists of a dry bead, a sample incubation buffer (Reagent A), and a detection buffer (Reagent B) containing a TSH receptor chimera (as disclosed in U.S. Patent Application Publication No. 2009/0325310 A1 published Dec. 31, 2009) conjugated to AP.

Abbreviations:
L=liter(s)
IU=international units
KCPS=kilocount(s) per second
Citrate buffer=100 mM sodium citrate, 100 mM NaCl, 10 mM magnesium acetate, 1 mM zinc chloride, 0.5% BSA, 0.1% mouse IgG, 0.2% PLURONIC® F68, 10% glycerol, pH 6.0-6.8
BSA=bovine serum albumin
IgG=immunoglobulin
MES: 2-(N-morpholino)ethanesulfonic acid
MES buffer=100 mM MES, 100 mM NaCl, 10 mM magnesium acetate, 1 mM zinc chloride, 0.5% BSA, 0.1% mouse IgG, 0.2% PLURONIC® F68, 10% glycerol, pH 6.0-6.8
PIPES buffer=100 mM PIPES, 100 mM NaCl, 10 mM magnesium acetate, 1 mM zinc chloride, 0.5% BSA, 0.1% mouse IgG, 0.2% PLURONIC® F68, 10% glycerol, pH 6.0-6.8

Example 1

Coating TSH Receptor on Beads

Polystyrene beads are incubated overnight with a buffer solution (100 mM sodium carbonate, 150 mM sodium chloride, 0.1% sodium azide, pH 9) of a monoclonal antibody (MAb) to TSH receptor. Following washes with the same buffer to remove excess MAb, beads are incubated for two hours with a buffer solution (100 mM PIPES, 2 mg/mL BSA, pH 6.8) of a TSH receptor chimera. Following washes with the same buffer to remove excess TSH receptor, the beads are incubated with 100 mM PIPES, 25 mg/mL BSA, 5% sucrose, pH 6.8 for one hour and then dried in a vacuum oven.

Example 2

Effect of HEDTA in TSH Receptor Buffer

Serum samples with varying amounts of native TSI were incubated for 30 minutes with a polystyrene bead having human TSH receptor chimera immobilized thereon as described in Example 1. Following centrifugal washes of the beads, a second TSH receptor chimera conjugated to alkaline phosphatase (AP) in a detection buffer (100 mM PIPES, 100 mM KCl, 1 mg/mL mouse IgG, 5 mg/mL BSA, 20% glycerol, pH 6.8) containing none (Control) or 1 mM HEDTA was added to the beads. After 30-minutes incubation, the beads were washed again, a substrate solution for AP was added and the signal was detected with a luminometer. The signal was measured when detection buffer was first prepared and after storage at 37° C. for 2 days. Table 1 shows the percent (%) signal for the various samples at day 0 and day 2.

TABLE 1

| Reagent TSI (IU/L) | Control | 1 mM HEDTA |
|---|---|---|
| Signal at Day 0 (KCPS) | | |
| 0 | 459 | 43 |
| 0.9 | 502 | 160 |
| 4.6 | 582 | 579 |
| 39.9 | 1474 | 3693 |
| AP Counts | 5651 | 6275 |
| Signal at Day 2 (KCPS) | | |
| 0 | 247 | 41 |
| 0.9 | 239 | 134 |
| 4.6 | 252 | 364 |
| 39.9 | 236 | 2439 |
| AP Counts | 5167 | 6548 |
| Signal Recovery at Day 2 (%) | | |
| 0 | 54% | 97% |
| 0.9 | 47% | 84% |
| 4.6 | 43% | 63% |
| 39.9 | 16% | 66% |
| AP Activity | 91% | 104% |

The reagent with 1 mM HEDTA showed nearly an order of magnitude lower non-specific binding (signal for zero TSI sample) and two fold higher signal than the control reagent at day 0 for the sample with the highest TSI concentration. The reagent containing HEDTA retained 66% of its activity compared to only 16% for the control reagent. The AP enzymatic activity varied slightly between 91% and 104% for the two reagents, which demonstrates that the enhanced activity retention was due to improved stability of the TSH receptor in the presence of HEDTA in accordance with the principles described herein and not to improved stability of AP.

Example 3

Effect of Glycerol in TSH Receptor Buffer

A TSH receptor chimera conjugated to AP (prepared as described above) was dissolved in detection buffers (0.1 M PIPES, 5 mM magnesium acetate, 0.5 mM zinc chloride, 1 mM HEDTA, 5 mg/mL BSA, 10 mg/mL casein, 2.5 µg/mL Amphotericin B, 0.2 mg/mL gentamycin sulfate) containing various concentrations of glycerol. The detection buffers were evaluated when first prepared and after storage at 37° C. for 7 days. Table 2 shows the percent (%) of initial signal retained after 7 days for the various reagents.

TABLE 2

| | Glycerol Amounts | | | |
|---|---|---|---|---|
| TSI (IU/L) | 20% | 30% | 40% | 50% |
| | Percent (%) Response Retained after 7 Days at 37° C. | | | |
| 0.00 | 97% | 114% | 106% | 105% |
| 0.18 | 73% | 102% | 103% | 106% |
| 0.37 | 70% | 98% | 104% | 101% |
| 0.77 | 66% | 97% | 109% | 103% |
| 1.59 | 67% | 102% | 100% | 97% |
| 3.36 | 68% | 104% | 109% | 104% |
| 6.84 | 59% | 93% | 102% | 108% |
| 13.73 | 57% | 94% | 109% | 104% |

TABLE 2-continued

| | Glycerol Amounts | | | |
|---|---|---|---|---|
| TSI (IU/L) | 20% | 30% | 40% | 50% |
| | Percent (%) Response Retained after 7 Days at 37° C. | | | |
| 26.39 | 54% | 85% | 101% | 103% |
| 50.71 | 51% | 77% | 90% | 100% |
| Average | 66% | 96% | 103% | 103% |

The stability of the detection receptor, as indicated by the retained signal, improved from 66% to nearly 100% as the glycerol content of the reagent increased from 20% to 50%.

Example 4

Effect of HEDTA Concentration in TSH Receptor Buffer

A TSH receptor chimera conjugated to AP (prepared as described above) was dissolved in a buffer (0.1 M PIPES, 5 mM magnesium acetate, 0.5 mM zinc chloride, 5 mg/mL BSA, 10 mg/mL casein, 30% glycerol, 2.5 µg/mL Amphotericin B, 0.2 mg/mL gentamycin sulfate) containing various concentrations of HEDTA. Table 3 shows the signal (KCPS) obtained for the various samples at various HEDTA concentrations.

TABLE 3

| | HEDTA (mM) | | | | | |
|---|---|---|---|---|---|---|
| TSI (IU/L) | 0.1 | 0.5 | 0.75 | 1.0 | 1.25 | 2 |
| 0 | 17 | 21 | 19 | 17 | 15 | 15 |
| 0.58 | NA | 925 | 929 | 953 | 872 | 957 |
| 9.26 | 288 | 1865 | 1939 | 2051 | 1883 | 1942 |
| AP | 16674 | 17192 | 14457 | 14704 | 14767 | 13772 |

The signal for the highest TSI sample increased dramatically as the HEDTA concentration increased. The alkaline phosphatase (AP) activity decreased slightly at higher HEDTA concentration, which demonstrates that the increased signal at higher HEDTA concentration is due to higher retained activity of the receptor and not AP activity.

Example 5

Effect of TSH Receptor in a Chelating Buffer

A TSH receptor chimera conjugated to alkaline phosphatase (prepared as described above) was dissolved in various buffers (MES, PIPES, Citrate) at various pH levels. All of the buffer formulations contained 10% glycerol as described above. FIG. 1 shows the signal for a sample having 33 IU/L of TSI. The signal varied from 2000 KCPS to 4000 KCPS for the various buffers at various pH levels.

Figure 2:
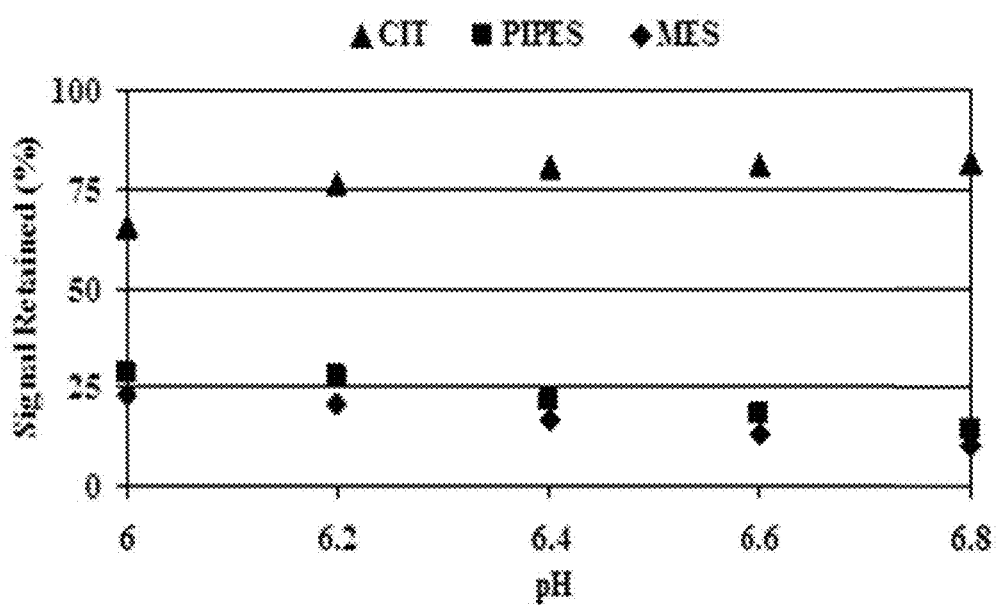
FIG. 2 is a graph depicting a plot of percent signal retained versus pH for the conjugate solutions of FIG. 1 after storage at 37° C. for one day.

FIG. 2 shows the percent signal retained after storing the detection buffers with the receptor at 37° C. for one day. The MES and PIPES buffers, which are not in accordance with the principles described herein, retained 25% or less of initial signal regardless of the pH. The Citrate buffer, in accordance with the principles described herein, retained between 65% and 80% of the initial signal.

Although the foregoing invention has been described in some detail by way of illustration and example for purposes of clarity of understanding, it will be readily apparent to those of ordinary skill in the art in light of the teachings in accordance with the principles described herein that certain changes and modifications may be made thereto without departing from the spirit or scope of the appended claims. Furthermore, the foregoing description, for purposes of explanation, used specific nomenclature to provide a thorough understanding of the examples. It will be apparent to one skilled in the art that the specific details are not required in order to practice the examples described herein. Thus, the foregoing descriptions of specific examples in accordance with the principles described herein are presented for purposes of illustration and description; they are not intended to be exhaustive or to limit the examples to the precise forms disclosed. Many modifications and variations are possible in view of the above teachings. The examples were chosen in order to explain the principles described herein and their practical applications and to thereby enable others skilled in the art to utilize the teachings.

What is claimed is:

1. A method of stabilizing a liquid solution of a thyroid stimulating hormone receptor, the method comprising:
    combining a liquid solution comprising a thyroid stimulating hormone receptor with a stabilizing amount of both (i) a chelating agent selected from the group consisting of triacetic acid chelating agents and tetraacetic acid chelating agents and (ii) a C3-05 polyol, wherein the stabilizing amount of the chelating agent is about 0.1 mM to about 2 mM and the stabilizing amount of the C3-05 polyol is about 20% to about 50% by weight, the stabilized liquid solution of the thyroid stimulating hormone receptor having a half-life of at least about 20 months during storage at a temperature of about 2° C. to about 40° C.

2. The method according to claim 1 wherein the thyroid-stimulating hormone receptor is a thyroid stimulating hormone receptor chimera bound to a support or a label.

3. The method according to claim 1 wherein the chelating agent is selected from the group consisting of N-(2-hydroxyethyl)-ethylenediamine-N,N',N'-triacetic acid and its salts, ethylene diamine tetraacetic acid and its salts, and ethylene glycol tetraacetic acid and its salts.

4. The method according to claim 1 wherein the stabilizing amount of chelating agent in the liquid solution is about 1 mM, and wherein the stabilized liquid solution of the thyroid stimulating hormone receptor retains at least about 60% of an initial receptor signal after 2 days of storage at 37° C.

5. The method according to claim 1 wherein the stabilizing amount of C3-05 polyol is about 30% to about 50% by weight, and wherein the stabilized liquid solution of the thyroid stimulating hormone receptor retains about 100% of an initial receptor signal after 7 days of storage at 37° C.

* * * * *